(12) United States Patent
Lee et al.

(10) Patent No.: US 10,561,393 B2
(45) Date of Patent: Feb. 18, 2020

(54) METHOD OF CALCULATING FEATURE OF BLOOD VESSEL AND ULTRASOUND APPARATUS FOR PERFORMING THE SAME

(71) Applicant: SAMSUNG MEDISON CO., LTD., Hongcheon-gun (KR)

(72) Inventors: Jin-yong Lee, Hongcheon-gun (KR); Sung-wook Park, Hongcheon-gun (KR); Jin-ki Park, Hongcheon-gun (KR); Joo-Hyun Song, Hongcheon-gun (KR); Bong-heon Lee, Hongcheon-gun (KR); Hyuk-Jae Chang, Seoul (KR); Namsik Chung, Seoul (KR); Geu-ru Hong, Seoul (KR); Jong-hwa Kim, Seoul (KR); Ji-hyun Yoon, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 1001 days.

(21) Appl. No.: 14/935,684

(22) Filed: Nov. 9, 2015

(65) Prior Publication Data
US 2016/0128667 A1 May 12, 2016

(30) Foreign Application Priority Data
Nov. 7, 2014 (KR) .......................... 10-2014-0154733

(51) Int. Cl.
*A61B 8/04* (2006.01)
*A61B 8/00* (2006.01)
(Continued)

(52) U.S. Cl.
CPC ............ *A61B 8/04* (2013.01); *A61B 5/02007* (2013.01); *A61B 8/0891* (2013.01); *A61B 8/463* (2013.01);
(Continued)

(58) Field of Classification Search
CPC ........... A61B 8/00; A61B 8/04; A61B 8/0891; A61B 8/463; A61B 8/467; A61B 8/54;
(Continued)

(56) References Cited

U.S. PATENT DOCUMENTS 7,081,091 B2 * 7/2006 Merrett ................ A61B 5/0205
600/300
2010/0113930 A1 5/2010 Miyachi
(Continued)

FOREIGN PATENT DOCUMENTS

JP 2006-122380 A 5/2006
JP 2008-302127 A 12/2008
(Continued)

OTHER PUBLICATIONS

Niki, Kiyomi, et al. "A noninvasive method of measuring wave intensity, a new hemodynamic index: application to the carotid artery in patients with mitral regurgitation before and after surgery." Heart and vessels 14.6 (1999): 263-271.*
(Continued)

*Primary Examiner* — Carolyn A Pehlke
(74) *Attorney, Agent, or Firm* — Sughrue Mion, PLLC

(57) ABSTRACT

Disclosed is an ultrasound apparatus. The ultrasound apparatus includes an ultrasound transceiver that transmits an ultrasound signal to an object and receives an ultrasound echo signal reflected from the object, a controller that detects a change amount of a diameter of a blood vessel of the object, based on the ultrasound echo signal, and a display unit that displays a blood pressure graph showing a blood pressure of the object and an image representing an inflection point in the blood pressure graph, based on the detected change amount of the diameter. The controller calculates a stiffness of the blood vessel, based on a blood pressure corresponding to the inflection point.

16 Claims, 12 Drawing Sheets

(51) Int. Cl.
*A61B 5/02* (2006.01)
*A61B 8/08* (2006.01)
*G06T 7/00* (2017.01)
*A61B 8/06* (2006.01)

(52) U.S. Cl.
CPC ............... *A61B 8/467* (2013.01); *A61B 8/54* (2013.01); *G06T 7/0012* (2013.01); *A61B 8/06* (2013.01); *A61B 8/5223* (2013.01)

(58) Field of Classification Search
CPC ......... A61B 8/06; A61B 8/5223; A61B 8/461; A61B 8/465; A61B 8/469; A61B 8/48; A61B 8/485; A61B 8/5215; G01S 7/52084; G06T 7/0012
See application file for complete search history.

(56) References Cited

U.S. PATENT DOCUMENTS

| | | | |
|---|---|---|---|
| 2011/0270051 A1 | 11/2011 | Naghavi et al. | |
| 2011/0319771 A1* | 12/2011 | Tsukahara | A61B 5/02007 600/485 |
| 2012/0232387 A1* | 9/2012 | Miyachi | A61B 5/02007 600/438 |
| 2012/0296223 A1 | 11/2012 | Fujii et al. | |
| 2014/0079729 A1 | 3/2014 | Kalidindi | |
| 2015/0289836 A1* | 10/2015 | Mizukami | A61B 8/04 600/438 |

FOREIGN PATENT DOCUMENTS

| | | |
|---|---|---|
| KR | 10-0877207 B1 | 1/2009 |
| WO | 2014/091999 A1 | 4/2016 |

OTHER PUBLICATIONS

Math is Fun (Second Derivative, https://www.mathsisfun.com/calculus/second-derivative.html; retrieved Jul. 9, 2019).*

Max and Min's, Second Derivative Test (http://clas.sa.ucsb.edu/staff/lee/Max%20and%20Min's.htm, retrieved Jul. 9, 2019).*

S J Vermeersch, et al., "Determining carotid artery pressure from scaled diameter waveforms: comparison and validation of calibration techniques in 2026 subjects", Physiological Measurement, vol. 29, No. 11, Nov. 1, 2008, pp. 1267-1280.

Yli-Ollila Heikki, et al., "Relation of arterial stiffness and axial motion of the carotid artery wall—a pilot study to test our motion tracking algorithm in practice", 36th Annual International Conference of the IEEE Engineering in Medicine and Biology Society, Aug. 26, 2014, pp. 246-249.

Communication from the European Patent Office dated Apr. 7, 2016 in a counterpart European Application No. 15190586.6.

* cited by examiner

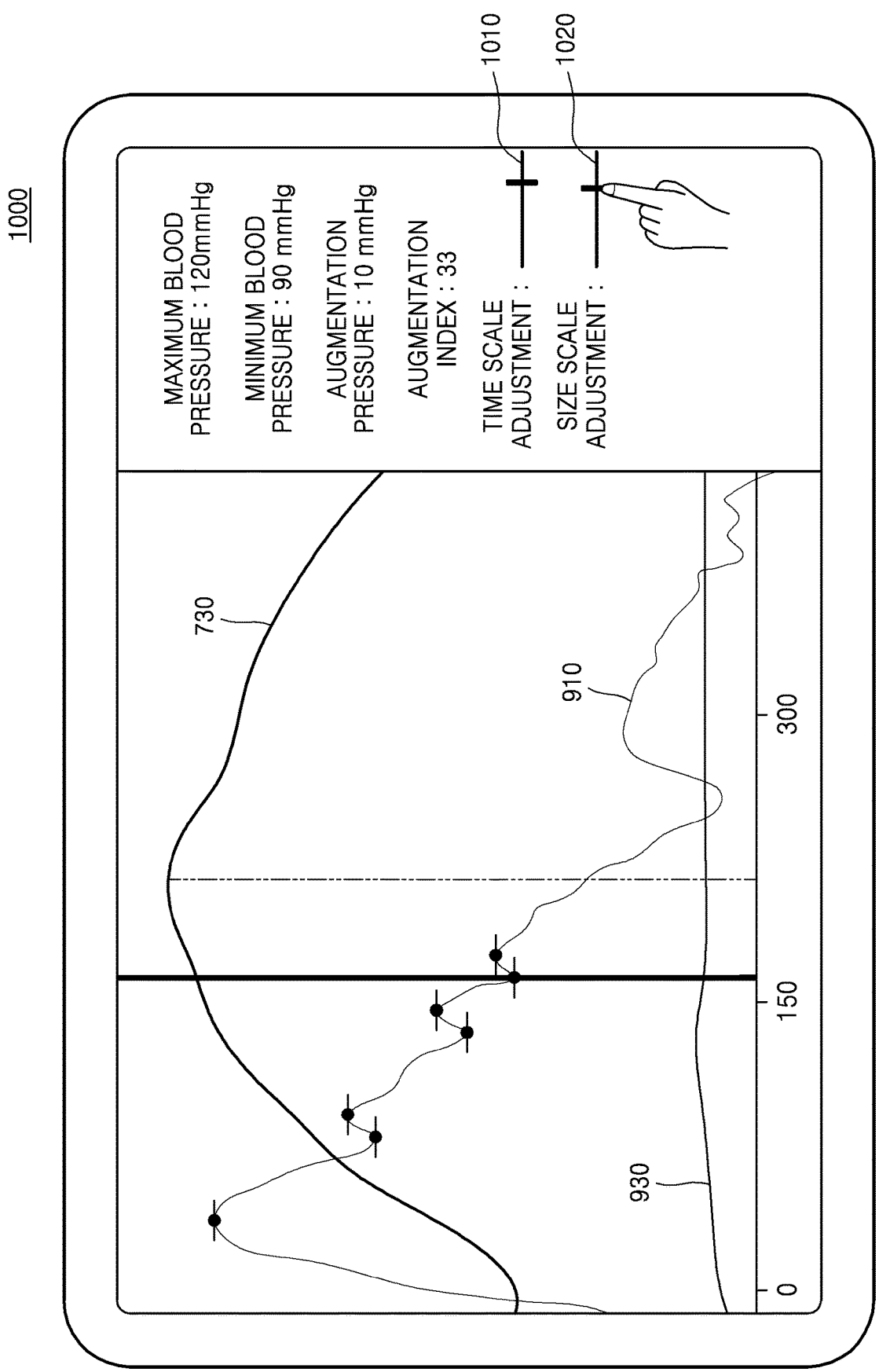

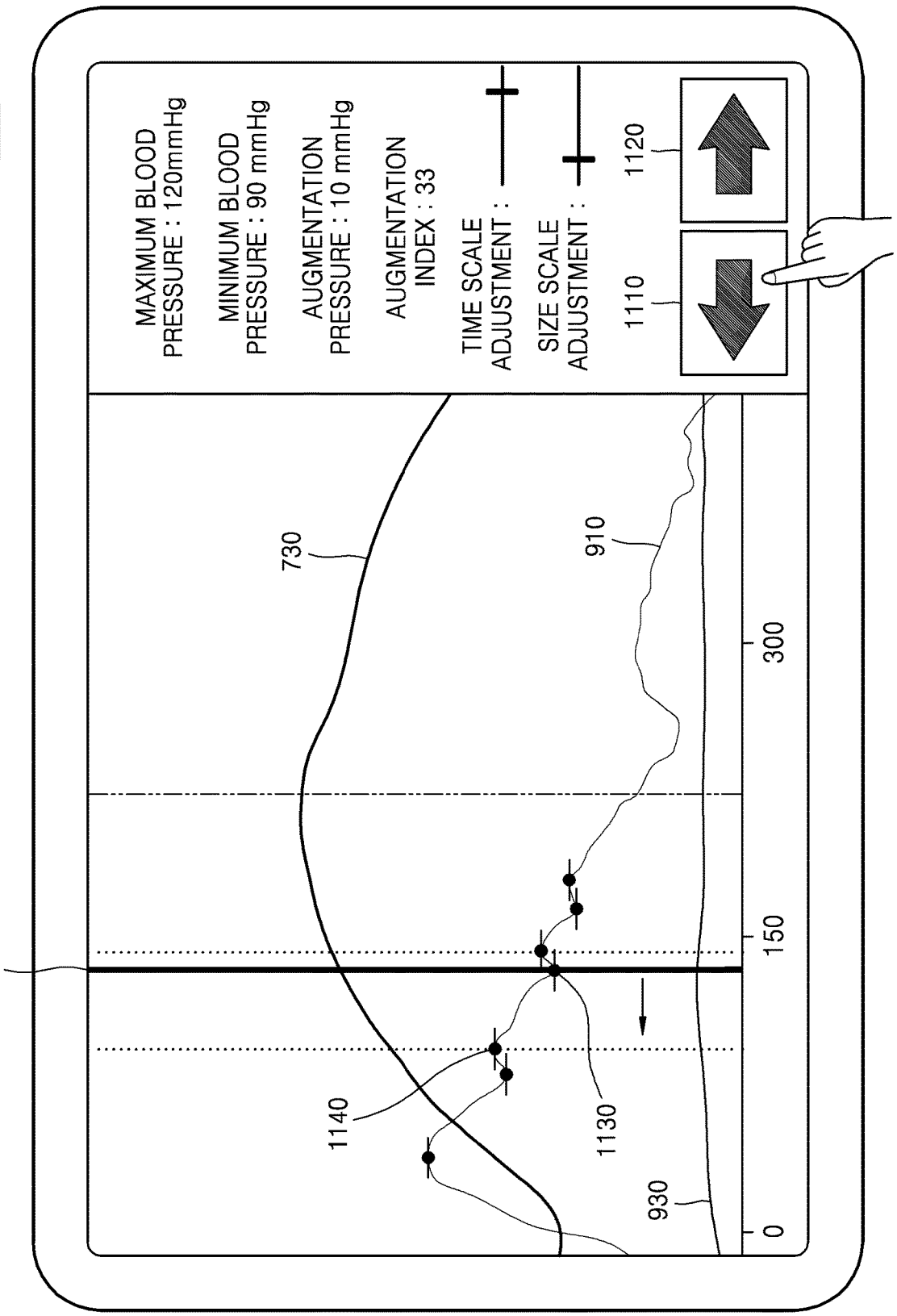

METHOD OF CALCULATING FEATURE OF BLOOD VESSEL AND ULTRASOUND APPARATUS FOR PERFORMING THE SAME

RELATED APPLICATION

This application claims the benefit of Korean Patent Application No. 10-2014-0154733, filed on Nov. 7, 2014, in the Korean Intellectual Property Office, the disclosure of which is incorporated herein in its entirety by reference.

BACKGROUND

1. Field

One or more exemplary embodiments relate to a method of calculating a stiffness of an artery and an ultrasound apparatus for performing the same.

2. Description of the Related Art

Ultrasound apparatuses transmit ultrasound signals generated by transducers of a probe to an object and receive echo signals reflected from the object, thereby obtaining at least one image of an internal part of the object. In particular, ultrasound apparatuses are used for medical purposes including observation of the interior of an object, detection of foreign substances, and diagnosis of damage to the object. Such ultrasound apparatuses provide high stability, display images in real time, and are safe due to the lack of radioactive exposure, compared to X-ray apparatuses. Therefore, ultrasound apparatuses are widely used together with other image diagnosis apparatuses.

Ultrasound apparatuses transmit ultrasound signals generated by transducers of a probe to an object and receive echo signals reflected from the object, thereby obtaining at least one image of an internal part of the object. In particular, ultrasound apparatuses are used for medical purposes including observation of the interior of an object, detection of foreign substances, and diagnosis of damage to the object. Such ultrasound apparatuses provide high stability, display images in real time, and are safe due to the lack of radioactive exposure, compared to X-ray apparatuses. Therefore, ultrasound apparatuses are widely used together with other image diagnosis apparatuses.

Arteries are hardened by various causes such as aging, melituria, etc., and hardening of the arteries augments a blood pressure by increasing a transfer speed of a blood flow pulse and quickening a return to a central artery of a reflected wave. The augmentation of a blood pressure may cause various diseases. Therefore, it is required to accurately measure a stiffness of arteries.

SUMMARY

One or more exemplary embodiments include a method of calculating a stiffness of an artery, based on an ultrasound image.

Additional aspects will be set forth in part in the description which follows and, in part, will be apparent from the description, or may be learned by practice of the presented exemplary embodiments.

According to one or more exemplary embodiments, an ultrasound apparatus includes: an ultrasound transceiver that transmits an ultrasound signal to an object and receives an ultrasound echo signal reflected from the object; a controller that detects a change amount of a diameter of a blood vessel of the object, based on the ultrasound echo signal; and a display unit that displays a blood pressure graph showing a blood pressure of the object and an image representing an inflection point in the blood pressure graph, based on the detected change amount of the diameter, wherein the controller calculates a stiffness of the blood vessel, based on a blood pressure corresponding to the inflection point.

The inflection point may include at least one inflection point in the blood pressure graph, the ultrasound apparatus may further include a user input unit that receives a user input which selects one from the at least one inflection point, and the controller may calculate the stiffness of the blood vessel, based on a blood pressure corresponding to the selected inflection point.

The controller may acquire an in-systole maximum blood pressure and a diastole blood pressure of the object, calculate a diameter change graph showing a time-based change amount of the diameter, based on the detected change amount of the diameter, and calculate the blood pressure graph by changing the diameter change graph to the blood pressure graph, based on the acquired in-systole maximum blood pressure and diastole blood pressure.

The display unit may display a speed graph of the change amount of the diameter on the blood pressure graph.

The controller may calculate a diameter change graph showing a time-based change amount of the diameter, based on the detected change amount of the diameter and differentiate the diameter change graph to calculate the speed graph of the change amount of the diameter.

The display unit may display an image, representing a time of at least one inflection point in the blood pressure graph, on the speed graph of the change amount of the diameter.

The controller may determine a point, in which a slope of the speed graph of the change amount of the diameter becomes 0, as a point in which at least one inflection point in the blood pressure graph is positioned, and the display unit may display an image, representing the at least one inflection point, on the determined point.

The controller may calculate the stiffness of the blood vessel, based a difference value between a maximum blood pressure in the blood pressure graph and a blood pressure of the inflection point.

The display unit may display a reference line indicating an inflection point which is selected from the at least one inflection point in the blood pressure graph by a user, and when a user input which moves the reference line to the right or the left is received, the display unit may move the reference line to an inflection point adjacent to an inflection point in which the reference line is displayed, and displays the moved reference line.

The display unit may adjust and display at least one selected from a time scale and a size scale of the speed graph of the change amount of the diameter, based on a user input which changes a scale of the speed graph of the change amount of the diameter.

According to one or more exemplary embodiments, a method of calculating a stiffness of a blood vessel includes: transmitting an ultrasound signal to an object and receiving an ultrasound echo signal reflected from the object; detecting a change amount of a diameter of a blood vessel of the object, based on the ultrasound echo signal; displaying a blood pressure graph showing a blood pressure of the object and an image representing an inflection point in the blood pressure graph, based on the detected change amount of the diameter, calculating a stiffness of the blood vessel, based on a blood pressure corresponding to the inflection point.

The inflection point may include at least one inflection point in the blood pressure graph, and the calculating of the stiffness may include: receiving a user input which selects one from the at least one inflection point; and calculating the stiffness of the blood vessel, based on a blood pressure corresponding to the selected inflection point.

The method may further include acquiring an in-systole maximum blood pressure and a diastole blood pressure of the object, wherein the displaying of the blood pressure graph may include: calculating a diameter change graph showing a time-based change amount of the diameter, based on the detected change amount of the diameter; and calculating the blood pressure graph by changing the diameter change graph to the blood pressure graph, based on the acquired in-systole maximum blood pressure and diastole blood pressure.

The method may further include displaying a speed graph of the change amount of the diameter on the blood pressure graph.

The displaying of the speed graph may include: calculating a diameter change graph showing a time-based change amount of the diameter, based on the detected change amount of the diameter; differentiating the diameter change graph to calculate the speed graph of the change amount of the diameter; and displaying the calculated speed graph of the change amount of the diameter.

The displaying of the image may include displaying an image, representing a time of at least one inflection point in the blood pressure graph, on the speed graph of the change amount of the diameter.

The displaying of the image may include: determining a point, in which a slope of the speed graph of the change amount of the diameter becomes 0, as a point in which at least one inflection point in the blood pressure graph is positioned; and displaying an image, representing the at least one inflection point, on the determined point.

The calculating of the stiffness may include calculating the stiffness of the blood vessel, based a difference value between a maximum blood pressure in the blood pressure graph and a blood pressure of the inflection point.

The method may further include displaying a reference line indicating an inflection point which is selected from the at least one inflection point in the blood pressure graph by a user, wherein the receiving of the user input may include: receiving a user input which moves the reference line to the right or the left is received; and moving the reference line to an inflection point adjacent to an inflection point in which the reference line is displayed, based on the user input.

The displaying of the speed graph may include adjusting at least one selected from a time scale and a size scale of the speed graph of the change amount of the diameter, based on a user input which changes a scale of the speed graph of the change amount of the diameter.

BRIEF DESCRIPTION OF THE DRAWINGS

These and/or other aspects will become apparent and more readily appreciated from the following description of the exemplary embodiments, taken in conjunction with the accompanying drawings in which:

FIGS. 10A and 10B are diagrams illustrating a method in which an ultrasound apparatus adjusts a scale of a speed graph based on a user input, according to an exemplary embodiment;

FIG. 11 is a diagram illustrating a method in which an ultrasound apparatus selects an inflection point based on a user input, according to an exemplary embodiment.

DETAILED DESCRIPTION

Figure 1:
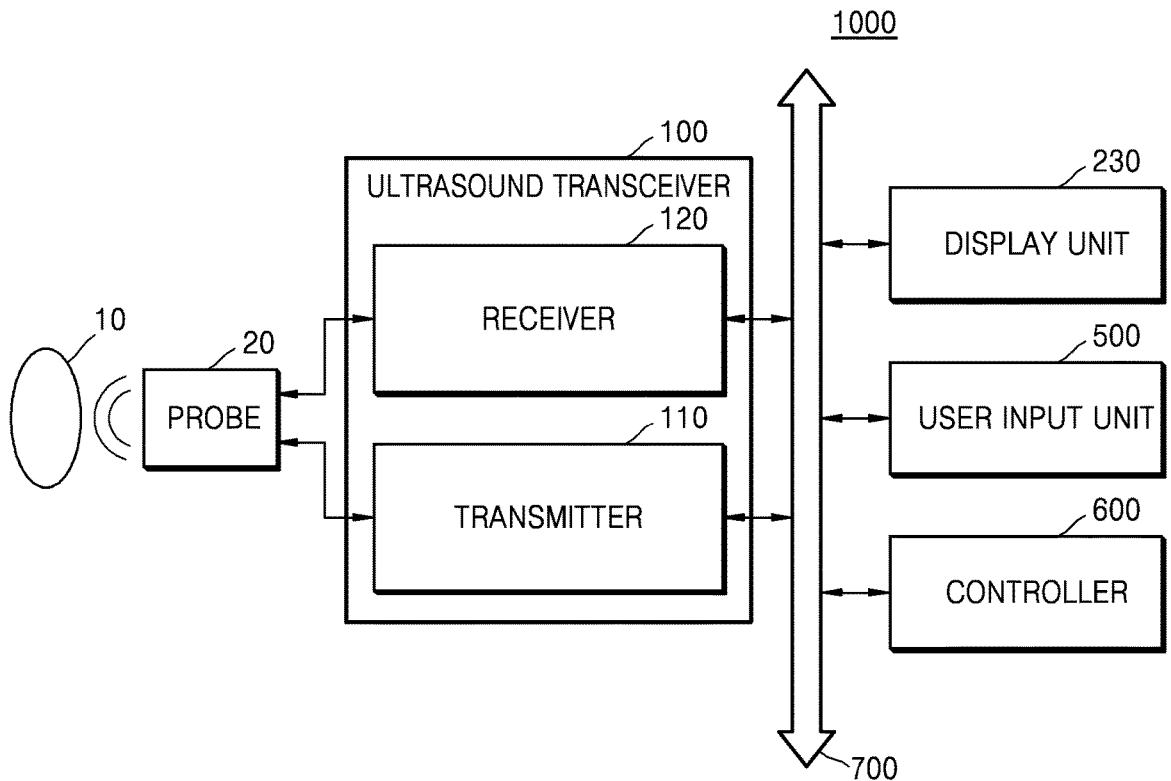
FIG. 1 is a diagram illustrating an ultrasound apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description.

Hereinafter, the terms used in the specification will be briefly defined, and the embodiments will be described in detail.

The terms used in this specification are those general terms currently widely used in the art in consideration of functions regarding the present invention, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

When a part "includes" or "comprises" an element, unless there is a particular description contrary thereto, the part can further include other elements, not excluding the other elements. In addition, terms such as " . . . unit", " . . . module", or the like refer to units that perform at least one function or operation, and the units may be implemented as hardware or software or as a combination of hardware and software.

Reference will now be made in detail to embodiments, examples of which are illustrated in the accompanying drawings. In this regard, the present embodiments may have different forms and should not be construed as being limited to the descriptions set forth herein. In the accompanying drawings, a portion irrelevant to a description of the inventive concept will be omitted for clarity. Moreover, like reference numerals refer to like elements throughout.

FIG. 1 is a diagram illustrating an ultrasound apparatus 1000 according to an exemplary embodiment.

Referring to FIG. 1, the ultrasound apparatus 1000 may include an ultrasound transceiver 100, a display unit 230, a user input unit 500, and a controller 600. The ultrasound transceiver 100, the display unit 230, the user input unit 500, and the controller 600 may be connected to each other through a bus 700. Also, the ultrasound transceiver 100 may include a transmitter 110 and a receiver 120. Also, according to an exemplary embodiment, the ultrasound apparatus 1000 may include a probe 20.

The ultrasound transceiver 100 may transmit an ultrasound signal to an object 10 and receive an ultrasound echo signal reflected from the object 10. For example, the ultrasound transceiver 100 may transmit the ultrasound signal to a main artery or a carotid artery of the object 10 and receive an ultrasound echo signal reflected from the main artery or carotid artery of the object 10.

The controller 600 may detect a change amount of a diameter of a blood vessel of the object 10, based on the ultrasound echo signal. For example, the controller 600 may acquire a plurality of ultrasound images representing the main artery or carotid artery of the object 10 during one period of a heartbeat of the object 10. Also, the controller 600 may detect, from the plurality of ultrasound images, a degree to which the diameter of the blood vessel of the object 10 is changed during the one period of the heartbeat.

Moreover, the controller 600 may calculate a blood flow graph showing a blood pressure of the object 10, based on the detected change amount of the diameter. For example, the controller 600 may calculate a diameter change graph showing a time-based change amount of the diameter, based on the detected change amount of the diameter. Also, the controller 600 may calculate a blood pressure graph by changing the diameter change graph to the blood pressure graph, based on an in-systole maximum blood pressure and a diastole blood pressure of the object 10.

Moreover, the controller 600 may calculate at least one inflection point in the blood pressure graph. For example, the controller 600 may differentiate the diameter change graph to calculate a speed graph of the change amount of the diameter. Also, the controller 600 may determine a point, in which a slope of the speed graph of the change amount of the diameter becomes 0, as a point in which at least one inflection point in the blood pressure graph is positioned.

The display unit 230 may display the calculated blood pressure graph and an image which represents at least one inflection point in the blood pressure graph.

The user input unit 500 may receive a user input which selects one from the at least one inflection point.

The controller 600 may calculate a stiffness of a blood vessel, based on a blood pressure corresponding to the selected inflection point.

Figure 2:
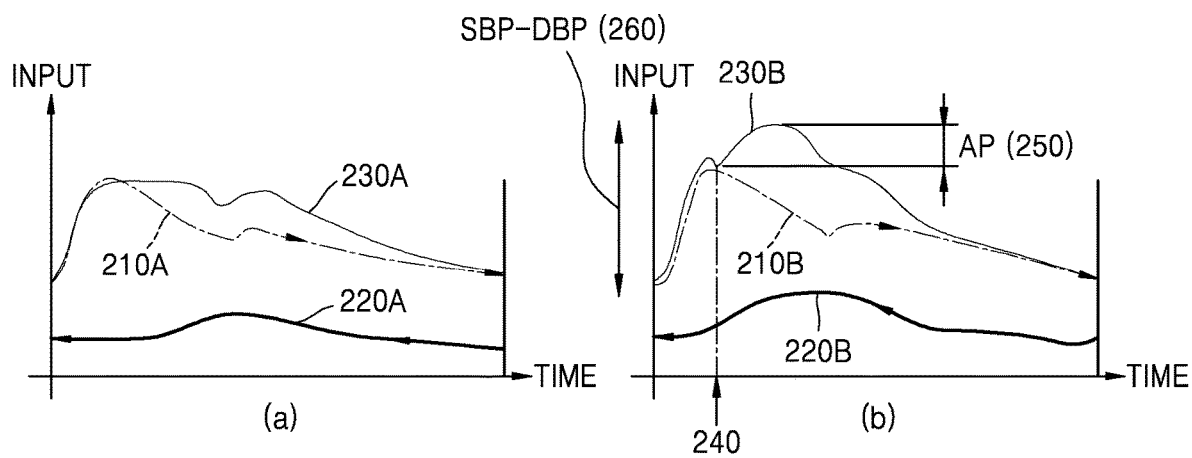
FIG. 2 is a diagram illustrating a blood pressure of an object detected by an ultrasound apparatus according to an exemplary embodiment.

FIG. 2 is a diagram illustrating a blood pressure of an object detected by the ultrasound apparatus 1000 according to an exemplary embodiment.

In one period of a heartbeat, as a heart contracts a forward wave that travels from the heart to a peripheral nerve is generated in an artery, and a reflected wave in which blood flow reaching the peripheral nerve is reflected to the heart is generated. At this time, when a blood vessel stiffens, a blood pressure augments because the forward wave meets the reflected wave in a systole section, and a systole blood pressure augments due to the augmented blood pressure.

Referring to FIG. 2, the ultrasound apparatus 1000 may detect a change in a blood pressure of an object. For example, the ultrasound apparatus 1000 may detect a change amount of a diameter of a blood vessel of the object and detect a change in a blood pressure, based on the detected change amount of the diameter. Also, the ultrasound apparatus 1000 may extract a speed component of blood flow in an artery by using Doppler and detect a change in the blood pressure of the object, based on the extracted speed component.

FIG. 2 (*a*) is a graph showing a blood pressure of a general artery which does not stiffen.

Referring to FIG. 2 (*a*), in a general artery in which a blood vessel does not stiffen, a blood pressure 230A of an artery may hardly augment even when a reflected wave 220A meets a forward wave 210A.

FIG. 2 (*b*) is a graph showing a blood pressure of a stiffened artery. Referring to FIG. 2 (*b*), in the blood pressure 230B of a stiffened artery, a speed of the reflected wave 220B which returns from a peripheral blood vessel to a heart may increase due to stiffening of a blood vessel. As the speed of the reflected wave 220B increases, the reflected wave 220B may quickly reach the artery in comparison with a general artery. As the reflected wave 220B quickly reaches the artery, in a state where the blood pressure augmented by the forward wave 210B is not sufficiently lowered in the artery, a systole blood pressure may augment by adding a blood pressure caused by the reflected wave 220B. In this case, the blood pressure graph 230B of the artery may have an inflection point at a time when the reflected wave 220B is added to the forward wave 210B. Also, a blood pressure 250 augmented by the reflected wave 220B may be referred to as an augmentation pressure caused by the reflected wave 220B.

Moreover, the ultrasound apparatus 1000 may determine a stiffness of a blood vessel, based on the augmentation pressure 250 caused by the reflected wave 220B. The augmentation pressure 250 caused by the reflected wave 220B may be calculated as a difference between a blood pressure at an inflection point and a maximum blood pressure in a systole. In detail, an accurate stiffness of a blood vessel may be calculated by normalizing the augmentation pressure 250, caused by the reflected wave 220B, to a total augmentation pressure 260. The total augmentation pressure 260 may denote a difference between the maximum blood pressure in the systole and a diastole blood pressure.

A value obtained by normalizing the augmentation pressure 250, caused by the reflected wave 220B, to the total augmentation pressure 260 may be referred to as a augmentation index (AI) and may be expressed as the following Equation (1):

$$AI = AP/(SBP - DBP) * 100 \qquad (1)$$

where SBP may denote a maximum blood pressure in the systole. Also, DBP may denote a diastole blood pressure. Also, AP may denote an augmentation pressure.

A blood pressure graph of an object may show a plurality of inflection points depending on a measurement method or a characteristic of an object. In this case, a user may select one from among the plurality of inflection points and calculate an augmentation index at the selected inflection point. Also, an inflection point may not remarkably be shown in a blood pressure graph of a human body.

Therefore, a position of an inflection point in a blood pressure graph is accurately calculated, and by displaying the calculated position of the inflection point, a diagnostician accurately selects a desired inflection point.

Figure 3:
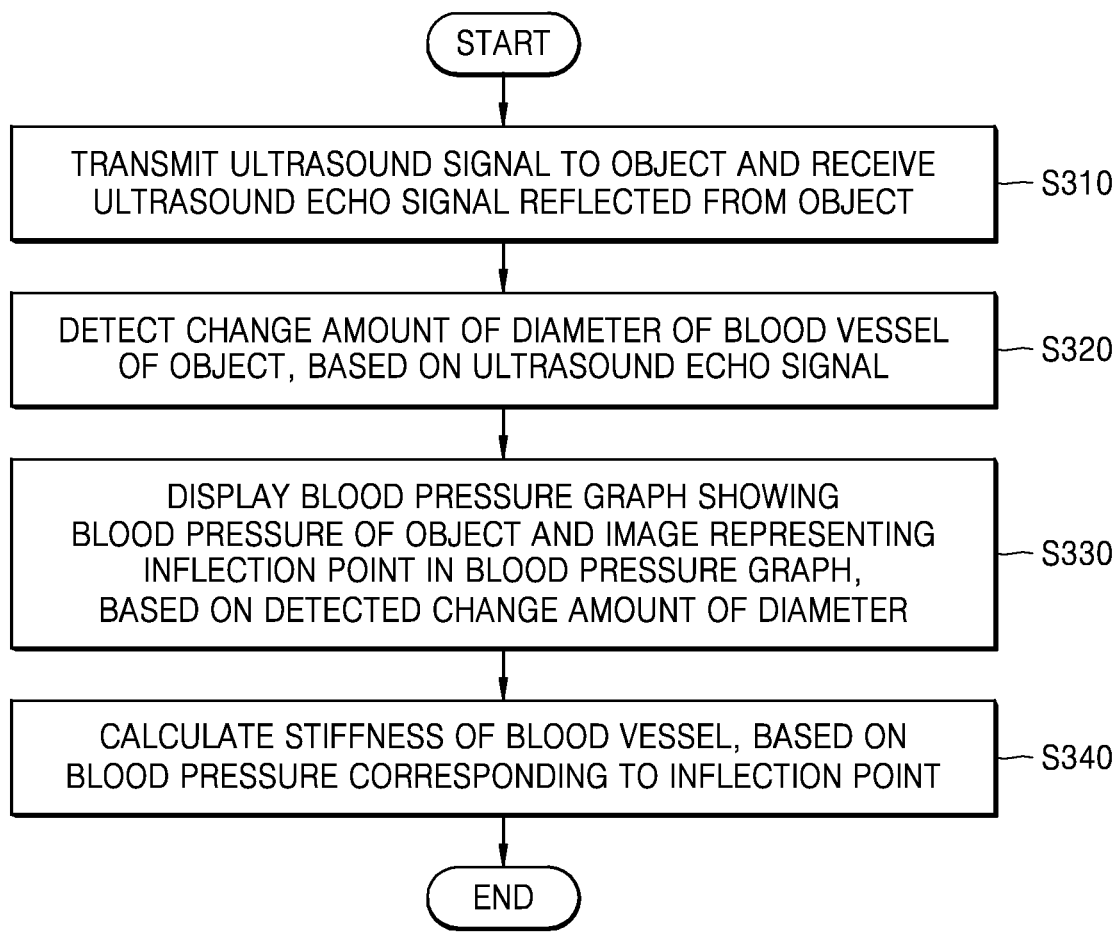
FIG. 3 is a diagram illustrating a method of calculating a stiffness of a blood vessel of an object, according to an exemplary embodiment.

FIG. 3 is a diagram illustrating a method of calculating a stiffness of a blood vessel of an object, according to an exemplary embodiment.

In operation S310, the ultrasound apparatus 1000 may transmit an ultrasound signal to an object and receive an ultrasound echo signal reflected from the object.

The ultrasound apparatus 1000 may transmit the ultrasound signal to a main artery or a carotid artery of the object and receive an ultrasound echo signal reflected from the main artery or carotid artery of the object.

In operation S320, the ultrasound apparatus 1000 may detect a change amount of a diameter of a blood vessel of the object, based on the ultrasound echo signal.

The ultrasound apparatus 1000 may acquire an ultrasound images representing the main artery or carotid artery of the object, based on the ultrasound echo signal. The ultrasound image may include a brightness (B) mode image, a motion (M) mode image, and a Doppler image, but is not limited thereto.

The ultrasound apparatus 1000 may acquire a plurality of ultrasound images representing the main artery or carotid artery of the object during one period of a heartbeat of the object. Also, the ultrasound apparatus 1000 may determine a position of a blood vessel in the plurality of ultrasound images.

Since the position of the blood vessel is determined, the ultrasound apparatus 1000 may detect a degree to which the diameter of the blood vessel of the object is changed during the one period of the heartbeat. For example, the ultrasound apparatus 1000 may calculate an increase amount or a decrease amount of the diameter with respect to a diameter at a time when a systole starts.

In operation S330, the ultrasound apparatus 1000 may display a blood pressure graph showing a blood pressure of the object and an image representing an inflection point in the blood pressure graph, based on the detected change amount of the diameter.

The ultrasound apparatus 1000 may calculate the blood pressure graph showing the blood pressure of the object, based on the detected change amount of the diameter. By using that a change amount of a blood pressure is proportional to a change amount of a diameter of a blood vessel, the ultrasound apparatus 1000 may calculate the blood pressure graph showing the blood pressure of the object, based on the change amount of the diameter of the blood vessel.

For example, the ultrasound apparatus 1000 may acquire an in-systole maximum blood pressure and a diastole blood pressure of the object. Also, the ultrasound apparatus 1000 may calculate a diameter change graph showing a time-based change amount of the diameter, based on the detected change amount of the diameter. Also, the ultrasound apparatus 1000 may calculate a blood pressure graph by changing the diameter change graph to the blood pressure graph, based on the acquired in-systole maximum blood pressure and diastole blood pressure. In this case, the ultrasound apparatus 1000 may change the diameter change graph to the blood pressure graph by expanding the diameter change graph, based on the in-systole maximum blood pressure and the diastole blood pressure.

Moreover, the ultrasound apparatus 1000 may determine a position of at least one inflection point in the blood pressure graph.

For example, the ultrasound apparatus 1000 may calculate the diameter change graph showing a time-based change amount of the diameter, based on the detected change amount of the diameter. The ultrasound apparatus 1000 may differentiate the diameter change graph to calculate a speed graph of the change amount of the diameter. Also, the ultrasound apparatus 1000 may determine a point, in which a slope of the speed graph of the change amount of the diameter becomes 0, as a point in which at least one inflection point in the blood pressure graph is positioned. The ultrasound apparatus 1000 may determine a point of the blood pressure graph, corresponding to the determined point, as an inflection point of the blood pressure graph.

As the blood pressure graph and the position of the at least one inflection point in the blood pressure graph are calculated, the ultrasound apparatus 1000 may display the blood pressure graph and an image representing the position of the at least one inflection point in the blood pressure graph.

Moreover, the ultrasound apparatus 1000 may display a speed graph of the change amount of the diameter on the blood pressure graph. In this case, the ultrasound apparatus 1000 may adjust at least one selected from a time scale and a size scale of the speed graph of the change amount of the diameter, based on a user input which changes a scale of the speed graph of the change amount of the diameter.

Moreover, the ultrasound apparatus 1000 may display an image, representing a time of the at least one inflection point in the blood pressure graph, on the speed graph of the change amount of the diameter.

Moreover, the ultrasound apparatus 1000 may display a reference line indicating an inflection point which is selected from the at least one inflection point in the blood pressure graph by a user.

The ultrasound apparatus 1000 may receive a user input which moves the reference line to the right or the left.

As the user input which moves the reference line to the right or the left is received, the reference line may be moved to an inflection point adjacent to an inflection point in which the reference line is displayed, and displayed.

In operation S340, the ultrasound apparatus 1000 may calculate a stiffness of a blood vessel, based on a blood pressure corresponding to an inflection point.

The ultrasound apparatus 1000 may calculate the stiffness of the blood vessel, based on a difference value between a maximum blood pressure in the blood pressure graph and a blood pressure of the selected inflection point. For example, the ultrasound apparatus 1000 may determine a blood pressure of an inflection point selected by the user. As the blood pressure of the inflection point is determined, the ultrasound apparatus 1000 may calculate an augmentation pressure caused by a reflected wave by subtracting the blood pressure of the inflection point from an in-systole maximum blood pressure. Also, the ultrasound apparatus 1000 may calculate a total augmentation pressure by subtracting a diastole blood pressure from the in-systole maximum blood pressure. As the augmentation pressure caused by the reflected wave and the total augmentation pressure are calculated, the ultrasound apparatus 1000 may calculate an augmentation index by subtracting the augmentation pressure caused by the reflected wave from the total augmentation pressure.

Figure 4:
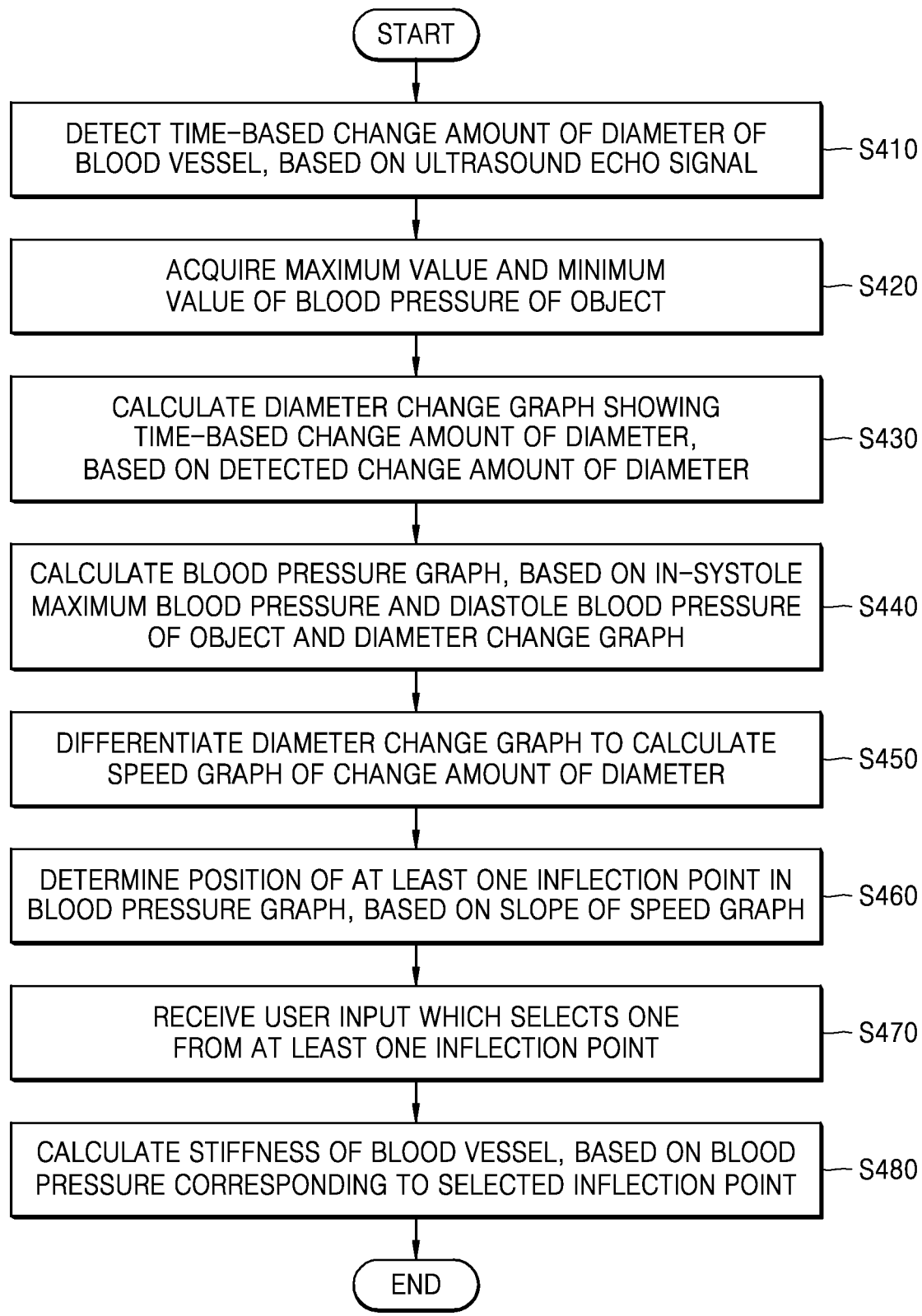
FIG. 4 is a diagram illustrating a method of calculating a stiffness of a blood vessel of an object, according to another exemplary embodiment.

FIG. 4 is a diagram illustrating a method of calculating a stiffness of a blood vessel of an object, according to another exemplary embodiment.

In operation S410, the ultrasound apparatus 1000 may detect a time-based change amount of a diameter of a blood vessel, based on an ultrasound echo signal.

The ultrasound apparatus 1000 may acquire a plurality of ultrasound images representing a main artery or a carotid artery of an object during one period of a heartbeat of the object. Also, the ultrasound apparatus 1000 may determine a position of a blood vessel in the plurality of ultrasound images. As the position of the blood vessel is determined, the ultrasound apparatus 1000 may detect a degree to which a diameter of the blood vessel of the object is changed during the one period of the heartbeat.

In operation S420, the ultrasound apparatus 1000 may acquire a maximum value and a minimum value of a blood pressure of the object.

The ultrasound apparatus 1000 may determine an in-systole maximum blood pressure and a diastole blood pressure which occur in the object during the one period of the heartbeat of the object. The maximum value and minimum value of the blood pressure in the one period of the heartbeat may be pre-stored in the ultrasound apparatus 1000. Also, the ultrasound apparatus 1000 may receive a user input which sets the in-systole maximum blood pressure and diastole blood pressure of the object. Also, the ultrasound apparatus 1000 may receive the maximum value and minimum value of the blood pressure of the object from a blood pressure measurement apparatus. The blood pressure measurement apparatus may include a digital cuff and a pulse wave measurer.

In operation S430, the ultrasound apparatus 1000 may calculate a diameter change graph showing the time-based change amount of the diameter, based on the detected change amount of the diameter.

The ultrasound apparatus 1000 may calculate the time-based change amount of the diameter during the one period of the heartbeat and calculate the diameter change graph showing the calculated change amount.

In operation S440, the ultrasound apparatus 1000 may calculate a blood pressure graph, based on the in-systole maximum blood pressure and diastole blood pressure of the object and the diameter change graph.

For example, the ultrasound apparatus 1000 may calculate the blood pressure by changing the diameter change graph to the blood graph, based on the acquired in-systole maximum blood pressure and diastole blood pressure. In this case, the ultrasound apparatus 1000 may change the diameter change graph to the blood pressure graph by expanding the diameter change graph, based on the in-systole maximum blood pressure and the diastole blood pressure. For example, the ultrasound apparatus 1000 may expand the diameter change graph of the blood vessel by adjusting a minimum value of the diameter change graph of the blood vessel to the diastole blood pressure and adjusting a maximum value of the diameter change graph of the blood vessel to the in-systole maximum blood pressure.

In operation S450, the ultrasound apparatus 1000 may differentiate the diameter change graph to calculate a speed graph of the change amount of the diameter.

The ultrasound apparatus 1000 may first-order differentiate the diameter change graph to calculate the speed graph of the change amount of the diameter. Also, the ultrasound apparatus 1000 may multi-order differentiate the diameter change graph to calculate the speed graph of the change amount of the diameter. In this case, the speed graph may represent an acceleration of the diameter change amount.

In operation S460, the ultrasound apparatus 1000 may determine a position of at least one inflection point in the blood pressure graph, based on a slope of the speed graph.

For example, the ultrasound apparatus 1000 may determine a point, in which the slope of the speed graph of the change amount of the diameter becomes 0, as a point in which at least one inflection point in the blood pressure graph is positioned. The ultrasound apparatus 1000 may determine a point of the blood pressure graph, corresponding to the determined point, as an inflection point of the blood pressure graph.

As the blood pressure graph and the position of the at least one inflection point in the blood pressure graph are calculated, the ultrasound apparatus 1000 may display the blood pressure graph and an image representing the at least one inflection point in the blood pressure graph.

In operation S470, the ultrasound apparatus 1000 may receive a user input which selects one from the at least one inflection point.

In operation S480, the ultrasound apparatus 1000 may calculate a stiffness of the blood vessel, based on a blood pressure corresponding to the selected inflection point.

Figure 5:
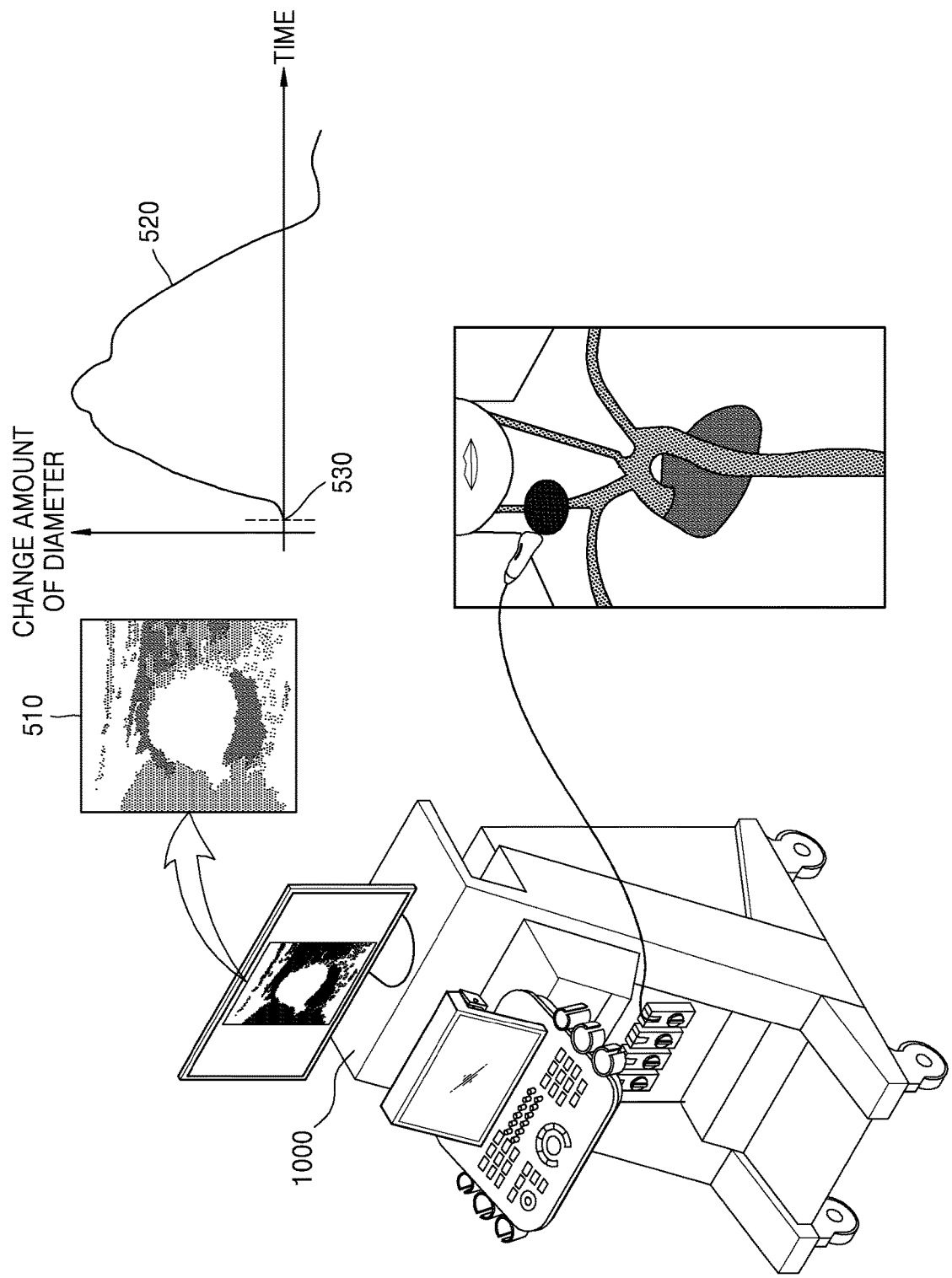
FIG. 5 is a diagram illustrating a method in which an ultrasound apparatus calculates a change amount of a diameter of a carotid artery of an object, according to an exemplary embodiment.

FIG. 5 is a diagram illustrating a method in which the ultrasound apparatus 1000 calculates a change amount of a diameter of a carotid artery of an object, according to an exemplary embodiment.

As blood spouts from a heart, a blood flow pulse may move along an artery. As the blood flow pulse moves along the artery, a flow pulsation, a pressure pulsation, and a diameter pulsation may occur along an artery which is spread in a whole body.

The flow pulsation may denote that as a blood flow pulse moves along an artery, a speed of blood flow in the artery is changed. Particularly, in an ascending artery, the speed of the blood flow may be changed by 300% of an average blood flow speed by the blood flow pulse. Therefore, the ultrasound apparatus 1000 may detect a movement of the blood flow pulse by measuring a speed of blood flow in an artery with a Doppler ultrasound probe.

Moreover, the pressure pulsation may denote that as the blood flow pulse moves along the artery, a blood pressure which is a side pressure applied to a blood vessel by the blood flow is changed.

Moreover, the diameter pulsation may denote that as the blood flow pulse moves along the artery, a diameter of the blood vessel is changed. A change amount of the diameter of the blood vessel may be proportional to a change amount of the blood pressure. A change in the diameter of the blood vessel may be clearly shown in a main artery or a carotid artery which is an elastic artery. Therefore, the ultrasound apparatus 100 may acquire a plurality of ultrasound images representing a time-based diameter of the carotid artery or the main artery, detect a change amount of a diameter of a blood vessel from the ultrasound images, and determine a time-based change amount of a blood pressure of an object, based on the change amount of the diameter of the blood vessel.

Referring to FIG. 5, the ultrasound apparatus 1000 may acquire a graph 520 showing a change amount of a diameter of a carotid artery during one period of a heartbeat, based on an ultrasound image 510 of the carotid artery of an object.

The ultrasound apparatus 1000 may generate a B mode image of the carotid artery of the object at certain time intervals. For example, the ultrasound apparatus 1000 may transmit an ultrasound signal to the carotid artery and generate the B mode image of the carotid artery, based on an ultrasound echo signal reflected from the carotid artery of the object.

As B mode image of the carotid artery is generated, the ultrasound apparatus 1000 may determine a position of the carotid artery in the B mode image of the carotid artery and determine a diameter of the carotid artery, based on the determined position of the carotid artery.

As the diameter of the carotid artery is determined, the ultrasound apparatus 1000 may acquire a change amount of the diameter of the carotid artery during the one period of the heartbeat. For example, the ultrasound apparatus 1000 may determine, as one period of a heartbeat, a period in which the diameter of the carotid artery increases once and then decreases. Also, the ultrasound apparatus 1000 may acquire, from an electrocardiogram (ECG) measurer, information about a period of the heartbeat of the object.

As the information about the period of the heartbeat is acquired, the ultrasound apparatus 1000 may calculate a change amount of the diameter, based on a reference diameter. The reference diameter may be a diameter of the carotid artery at a time 530 when a systole starts. Also, the reference diameter may be a minimum value of the diameter during the one period of the heartbeat. The ultrasound apparatus 1000 may calculate the diameter of the carotid artery with the elapse of time and calculate the change amount of the diameter by subtracting the reference diameter from the calculated diameter.

Moreover, the ultrasound apparatus 1000 may display, on a screen, the diameter change graph 520 of the carotid artery along with the ultrasound image 510 of the carotid artery in the one period of the heartbeat.

Figure 6:
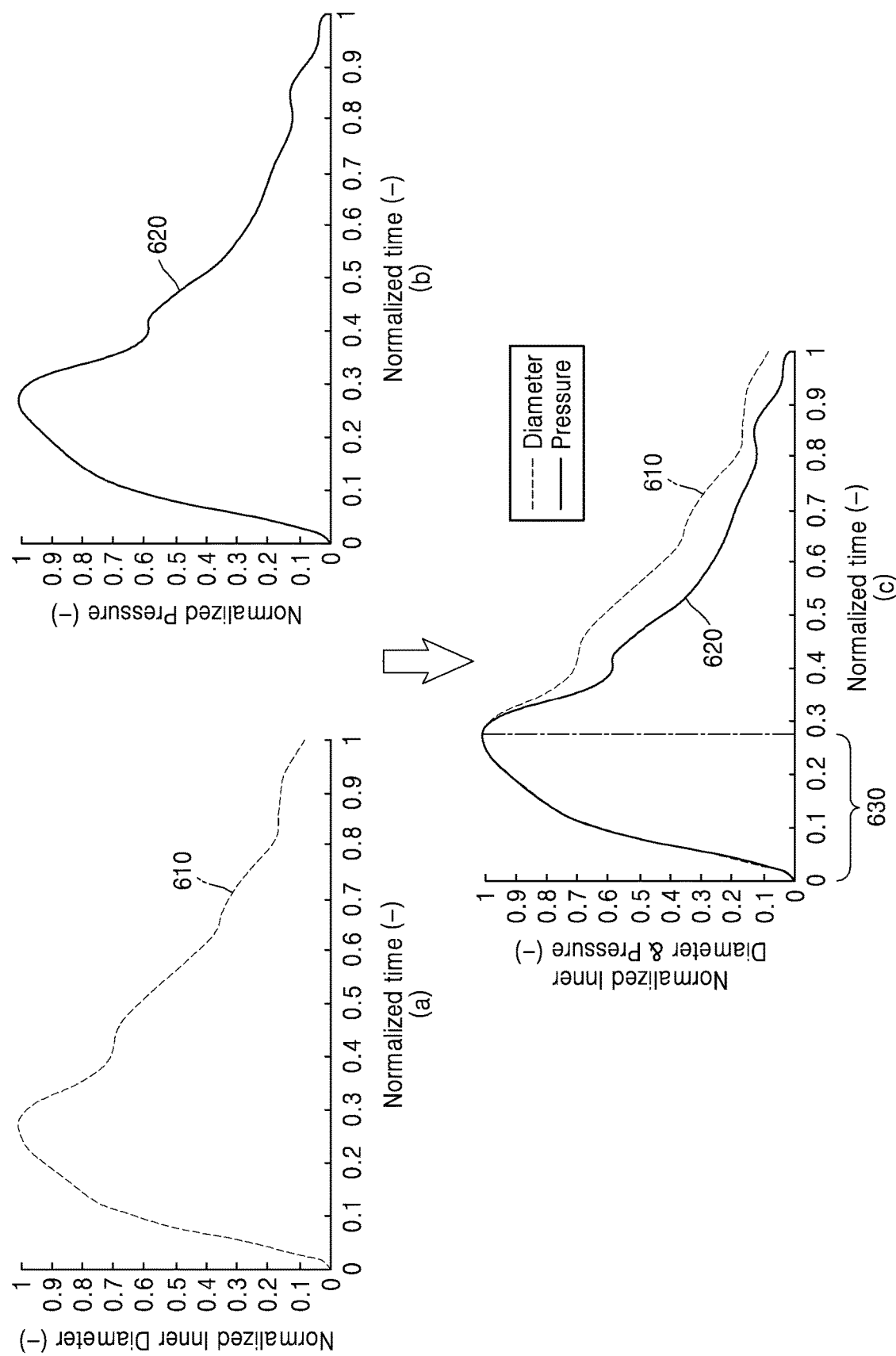
FIG. 6 is a diagram illustrating a method in which an ultrasound apparatus calculates a blood pressure graph based on a change amount of a diameter of a blood vessel, according to an exemplary embodiment.

FIG. 6 is a diagram illustrating a method in which the ultrasound apparatus 1000 calculates a blood pressure graph based on a change amount of a diameter of a blood vessel, according to an exemplary embodiment.

As a blood pressure augments or decreases, a diameter of a blood vessel may increase or decrease in proportion to an augmentation amount or a decrease amount of the blood pressure.

Referring to FIG. 6, FIG. 6 (*a*) shows a graph 610 in which a change amount of a diameter of a blood vessel during one period of a heartbeat is normalized. Also, FIG. 6 (*b*) shows a graph 620 in which a change amount of a blood pressure in the same time section of the same object is normalized. Also, FIG. 6 (*c*) shows a graph when the normalization graph 610 of the blood vessel overlaps the normalization graph 620 of the blood pressure.

Referring to FIG. 6 (*c*), the normalization graph 610 of the blood vessel may overlap the normalization graph 620 of the blood pressure. Particularly, the normalization graph 610 of the blood vessel and the normalization graph 620 of the blood pressure may show the same value in a systole section where an inflection point in which an augmentation index is calculated is positioned.

Therefore, the ultrasound apparatus 1000 may acquire a maximum blood pressure in a systole section and a diastole blood pressure of an object and acquire a blood pressure graph showing a blood pressure of the object by expanding or contracting the graph 520 of the change amount of the diameter of the blood vessel illustrated in FIG. 5, based on the acquired blood pressure. An exemplary embodiment in which a blood pressure graph showing a blood pressure of an object is acquired based on a change amount of a diameter of a blood vessel will be described in detail with reference to FIG. 7.

The ultrasound apparatus 1000 may calculate a position of an inflection point in the blood pressure graph from the graph 520 of the change amount of the diameter of the blood vessel. An inflection point in the graph 520 of the change amount of the diameter of the blood vessel may be determined. As the inflection point in the graph 520 of the change amount of the diameter of the blood vessel is determined, the ultrasound apparatus 1000 may determine a time of the determined inflection point as a time of the inflection point in the blood pressure graph. An exemplary embodiment in which a position of an inflection point in a blood pressure graph is acquired based on a change amount of a diameter of a blood vessel will be described in detail with reference to FIG. 8.

Figure 7:
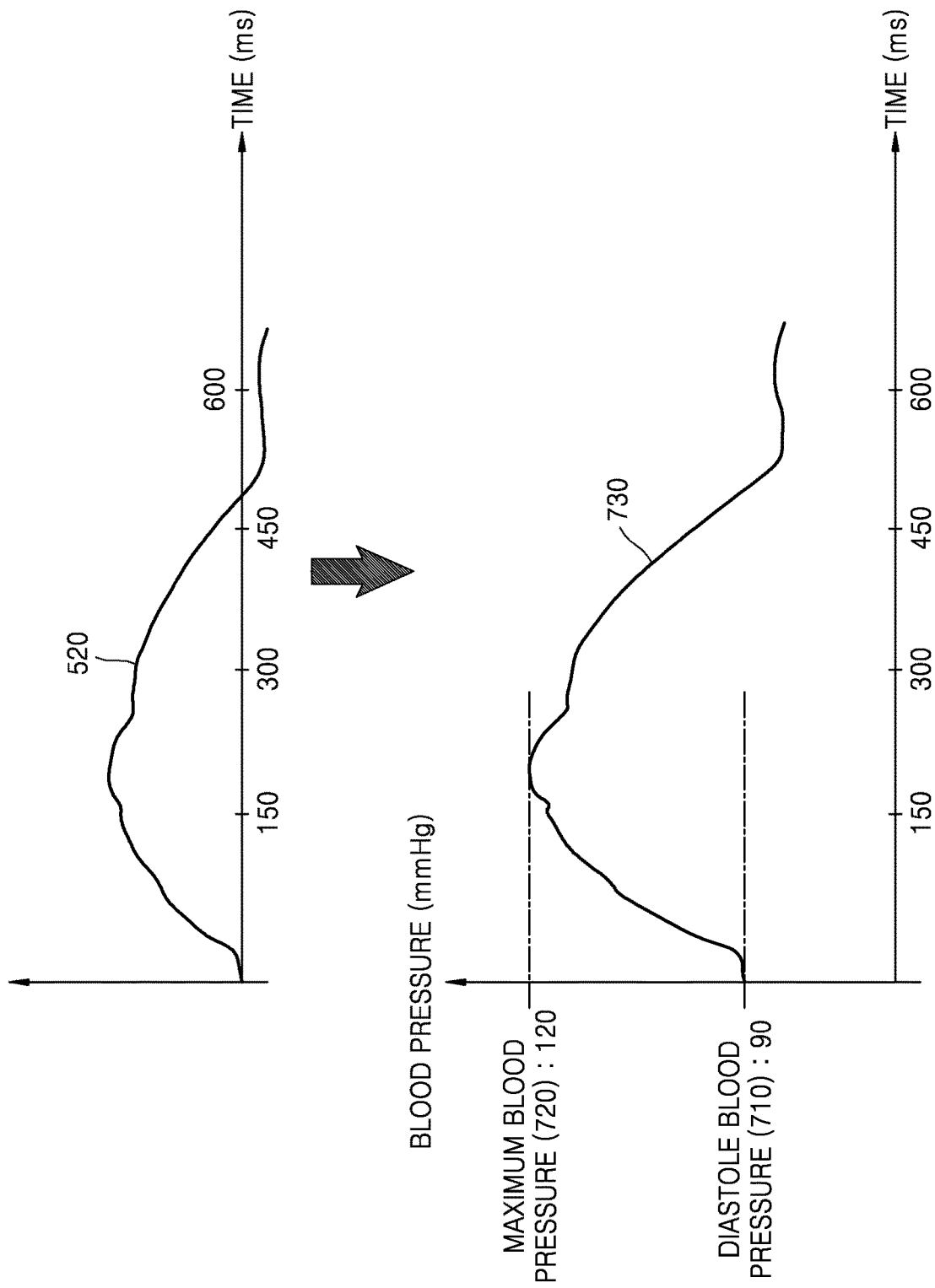
FIG. 7 is a diagram illustrating a method in which an ultrasound apparatus calculates a blood pressure graph based on a graph of a change amount of a diameter of a blood vessel, according to an exemplary embodiment.

FIG. 7 is a diagram illustrating a method in which the ultrasound apparatus 1000 calculates a blood pressure graph based on a graph 520 of a change amount of a diameter of a blood vessel, according to an exemplary embodiment.

Referring to FIG. 7, the ultrasound apparatus 1000 may determine a diastole blood pressure 710 and a maximum blood pressure 720 in a systole section, which occur in an object during one period of a heartbeat of the object. The diastole blood pressure 710 and the maximum blood pressure 720 in the systole section in the one period of the heartbeat may be pre-stored in the ultrasound apparatus 1000. Also, the ultrasound apparatus 1000 may receive a user input which sets the diastole blood pressure 710 of the object and the maximum blood pressure 720 of the object in the systole section. Also, the ultrasound apparatus 1000 may receive, from the blood pressure measurement apparatus, the diastole blood pressure 710 of the object and the maximum blood pressure 720 of the object in the systole section.

As the diastole blood pressure 710 of the object and the maximum blood pressure 720 of the object in the systole section are determined, the ultrasound apparatus 1000 may expand the diameter change graph 520 of the blood vessel by adjusting a minimum value of the diameter change graph 520 of the blood vessel to the diastole blood pressure 710 and adjusting a maximum value of the diameter change graph 520 of the blood vessel to the maximum blood pressure 720 in the systole section. As the diameter change graph 520 is expanded, the ultrasound apparatus 1000 may determine the expanded diameter change graph 520 of the blood vessel as a blood pressure graph showing a blood pressure in the one period of the heartbeat.

Figure 8:
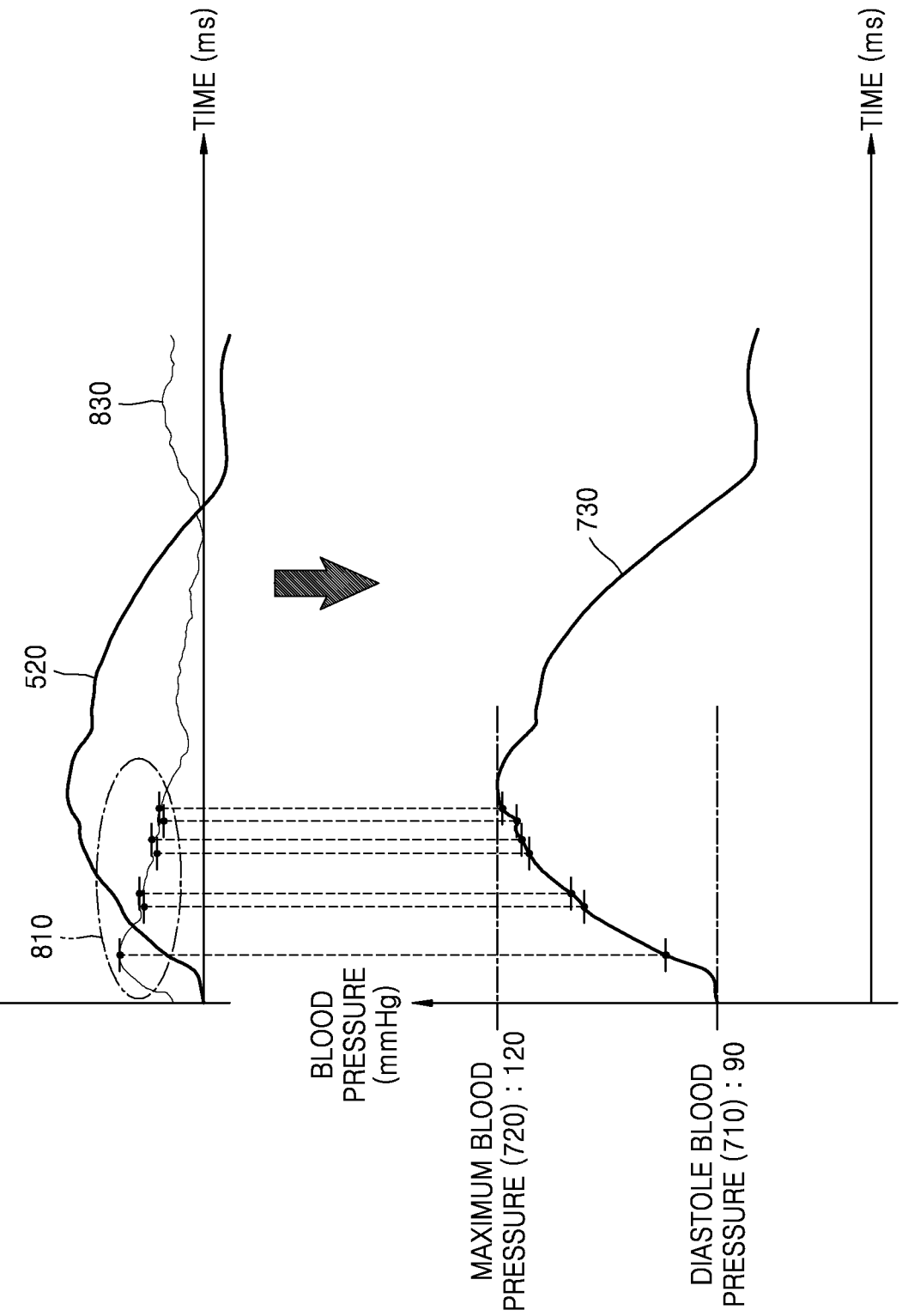
FIG. 8 is a diagram illustrating a method in which an ultrasound apparatus acquires a position of an inflection point in a blood pressure graph based on a graph of a change amount of a diameter of a blood vessel, according to an exemplary embodiment.

FIG. 8 is a diagram illustrating a method in which the ultrasound apparatus 1000 acquires a position of an inflection point in a blood pressure graph 730 based on a graph 520 of a change amount of a diameter of a blood vessel, according to an exemplary embodiment.

Referring to FIG. 8, the ultrasound apparatus 1000 may calculate an inflection point in the graph 520 of the change amount of the diameter of the blood vessel and determine a time of the calculated inflection point as a time of the inflection point in the blood pressure graph 730.

The ultrasound apparatus 1000 may differentiate the graph 520 of the change amount of the diameter of the blood vessel to calculate a speed graph 830 of the change amount of the diameter. The ultrasound apparatus 1000 may calculate the speed graph 830 of the change amount of the diameter through multi-order differentiation in addition to first-order differentiation. As the speed graph 830 of the change amount of the diameter is calculated, the ultrasound apparatus 1000 may determine the speed graph 830 of the change amount of the diameter as a speed graph of a blood pressure graph 730.

Moreover, the ultrasound apparatus 1000 may calculate points 810, in which a slope becomes 0, from among a plurality of points in the speed graph 810 and determine the calculated points 810 as inflection points of the graph 520 of the change amount of the diameter. Also, as positions of the inflection points 810 in the graph 520 of the change amount of the diameter are calculated, the ultrasound apparatus 1000 may determine a point, in which each of the inflection points 810 is positioned, as a point in which an inflection point is positioned in the blood pressure graph 730. For example, when inflections appear at 110 ms and 130 ms in the graph 520 of the change amount of the diameter of the blood vessel, the ultrasound apparatus 1000 may determine 110 ms and 130 ms as points in which inflection points in the blood pressure graph 730 appear.

Figure 9:
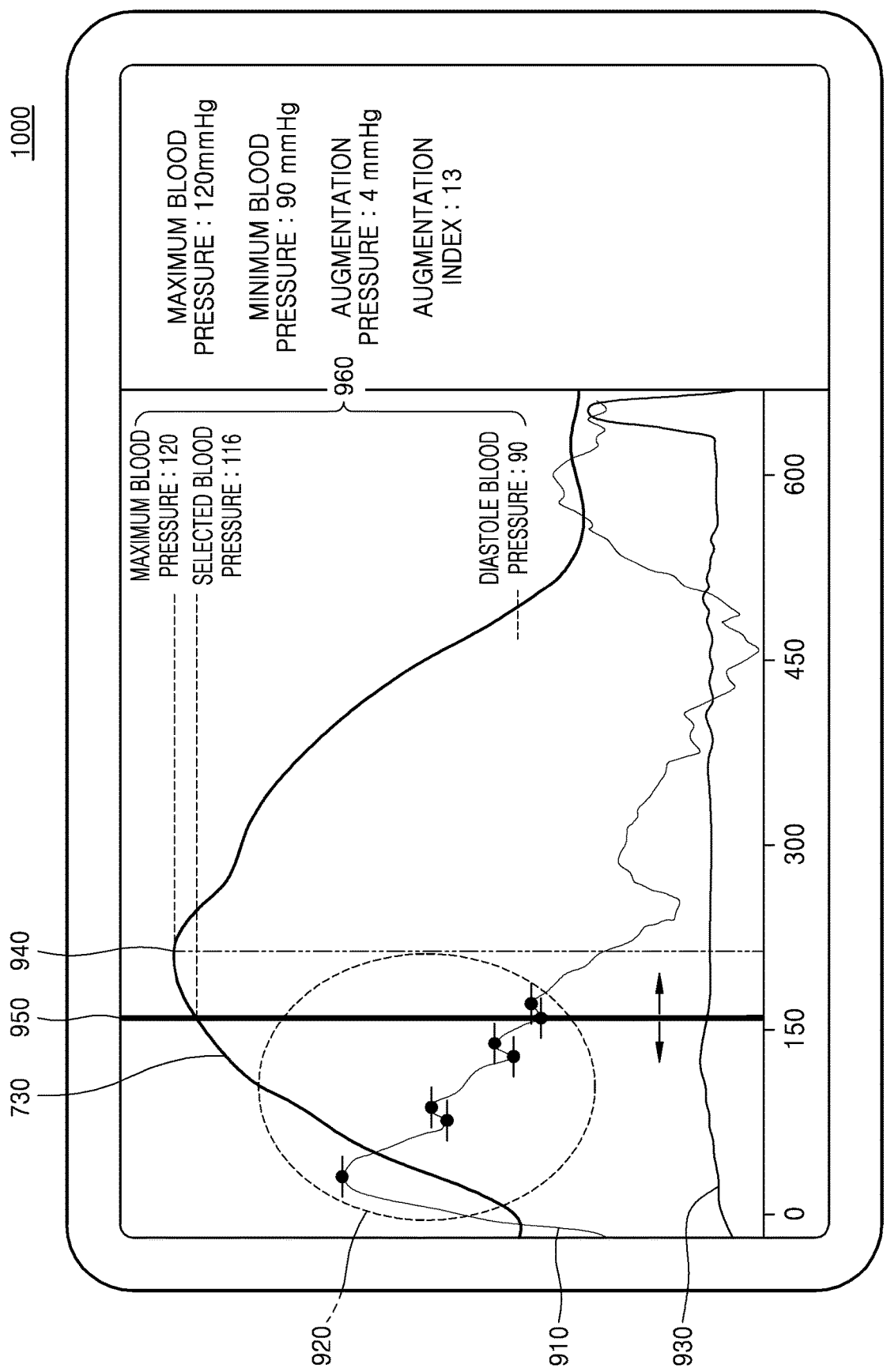
FIG. 9 is a diagram illustrating a method in which an ultrasound apparatus displays an inflection point in a blood pressure graph, according to an exemplary embodiment.

FIG. 9 is a diagram illustrating a method in which the ultrasound apparatus 1000 displays an inflection point in a blood pressure graph 730, according to an exemplary embodiment.

Referring to FIG. 9, the ultrasound apparatus 1000 may display the blood pressure graph 730. Also, the ultrasound apparatus 1000 may display a speed graph 910 on the blood pressure graph 730. Also, the ultrasound apparatus 1000 may display a plurality of images 920, representing a position of an inflection point of the blood pressure graph 730, on the speed graph 910.

The ultrasound apparatus 1000 may display the blood pressure graph 730 which is calculated based on a diameter change graph. Also, the ultrasound apparatus 1000 may display the speed graph 910 which is calculated by differentiating the diameter change graph on the blood pressure graph 730. In this case, the ultrasound apparatus 1000 may expand and display a size of the speed graph 910 so that a distance between the images 920 representing the position of the inflection point increases.

Moreover, when information about a heartbeat period of an object is received from the ECG apparatus, the ultrasound apparatus 1000 may display a graph 930 showing the heartbeat period along with the blood pressure graph 730 and the speed graph 910.

Moreover, the ultrasound apparatus 1000 may display an image 940 representing a point of a maximum value of a blood pressure in the blood pressure graph 730. Also, the ultrasound apparatus 1000 may display a reference line 950, representing a point selected by a user, on the blood pressure graph 730.

The ultrasound apparatus 1000 may move the reference line to the right or the left, based on a user input. For example, when a user input which laterally rotates a trackball connected to a control panel of the ultrasound apparatus 1000 is received, the ultrasound apparatus 1000 may move the reference line 950 to the right or the left. Also, when a user input which selects a right arrow key or a left arrow key is received, the ultrasound apparatus 1000 may move the reference line 950 by a certain distance to the right or the left. Also, when a user input which touches and drags the reference line 950 is received, the ultrasound apparatus 1000 may move the reference line 950 to the right or the left along a dragged region.

As the reference line 950 is moved to the right or the left, the ultrasound apparatus 1000 may calculate an augmentation pressure at the selected point and display the calculated augmentation pressure on a screen. Also, the ultrasound apparatus 1000 may calculate an augmentation index at the selected point and display the calculated augmentation index on a screen.

Moreover, the ultrasound apparatus 1000 may display, on the blood pressure graph 730, an image 960 which represents a maximum blood pressure of the object, a blood pressure at a point in which the reference line 950 is positioned, and a diastole blood pressure of the object.

Figure 10A:
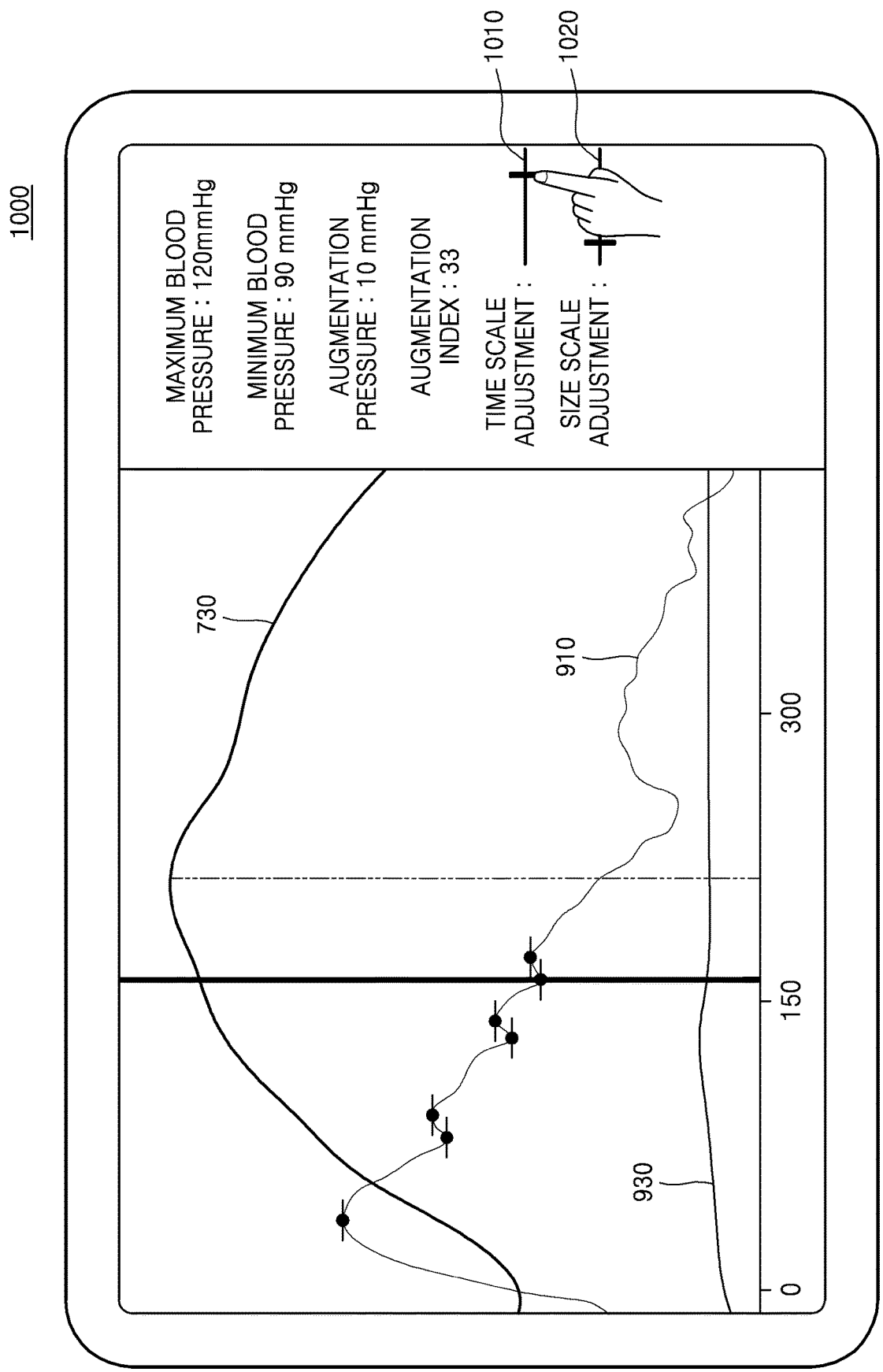

FIGS. 10A and 10B are diagrams illustrating a method in which the ultrasound apparatus 1000 adjusts a scale of a speed graph 910 based on a user input, according to an exemplary embodiment.

Referring to FIG. 10A, the ultrasound apparatus 1000 may adjust a time scale of a speed graph 910, based on a user input.

The ultrasound apparatus 1000 may display an interface object 1010 for adjusting the time scale of the speed graph 910. The interface object 1010 for adjusting the time scale may be an image in which a movement point is displayed on a horizontal straight line.

When a user input which moves the movement point in the interface object 1010 for adjusting the time scale is received, the ultrasound apparatus 1000 may change the time scale and display the speed graph 910. For example, when a user input which increases the time scale is received, the ultrasound apparatus 1000 may extend a horizontal axis which is a time axis, and increase a time scale of a graph 930 which shows a blood pressure graph 730, the speed graph 910, and a heartbeat period, based on the extended time axis.

Referring to FIG. 10B, the ultrasound apparatus 1000 may adjust a size scale of a speed graph 910, based on a user input.

The ultrasound apparatus 1000 may display an interface object 1020 for adjusting the size scale of the speed graph 910.

When a user input which moves a movement point in the interface object 1020 for adjusting the size scale is received, the ultrasound apparatus 1000 may change the size scale of the speed graph 910 and display the speed graph 910. For example, when a user input which increases the size scale is received, the ultrasound apparatus 1000 may expand and display the speed graph 910.

As a time scale or a size scale of a speed graph increases, a distance between inflection points increases. As the distance between the inflection points increases, a user selects an inflection point more precisely.

FIG. 11 is a diagram illustrating a method in which the ultrasound apparatus 1000 selects an inflection point based on a user input, according to an exemplary embodiment.

Referring to FIG. 11, the ultrasound apparatus 1000 may provide an interface for selecting one from among a plurality of pre-calculated inflection points.

The ultrasound apparatus 1000 may display a reference line 950 at a position of an inflection point which is selected from among a plurality of inflection points by a user. Also, the ultrasound apparatus 1000 may display a plurality of buttons 1110 and 1120 for selecting one from among the plurality of inflection points.

When a user input which selects the buttons 1110 and 1120 is received, the ultrasound apparatus 1000 may move the reference line 950 to an inflection point adjacent to an inflection point in which the reference line 950 is displayed. For example, when a user input which selects a left movement button 1110 is received, the ultrasound apparatus 1000 may move the reference line 950 from a first inflection point 1130, in which the reference line 950 is displayed, to a second inflection point 1140 which is positioned on the left of the first inflection point 1130.

As the reference line 950 is moved to the second inflection point 1140, the ultrasound apparatus 1000 may calculate an augmentation pressure and an augmentation index at the second inflection point 1140 and display the calculated augmentation pressure and augmentation index on a screen.

Figure 12:
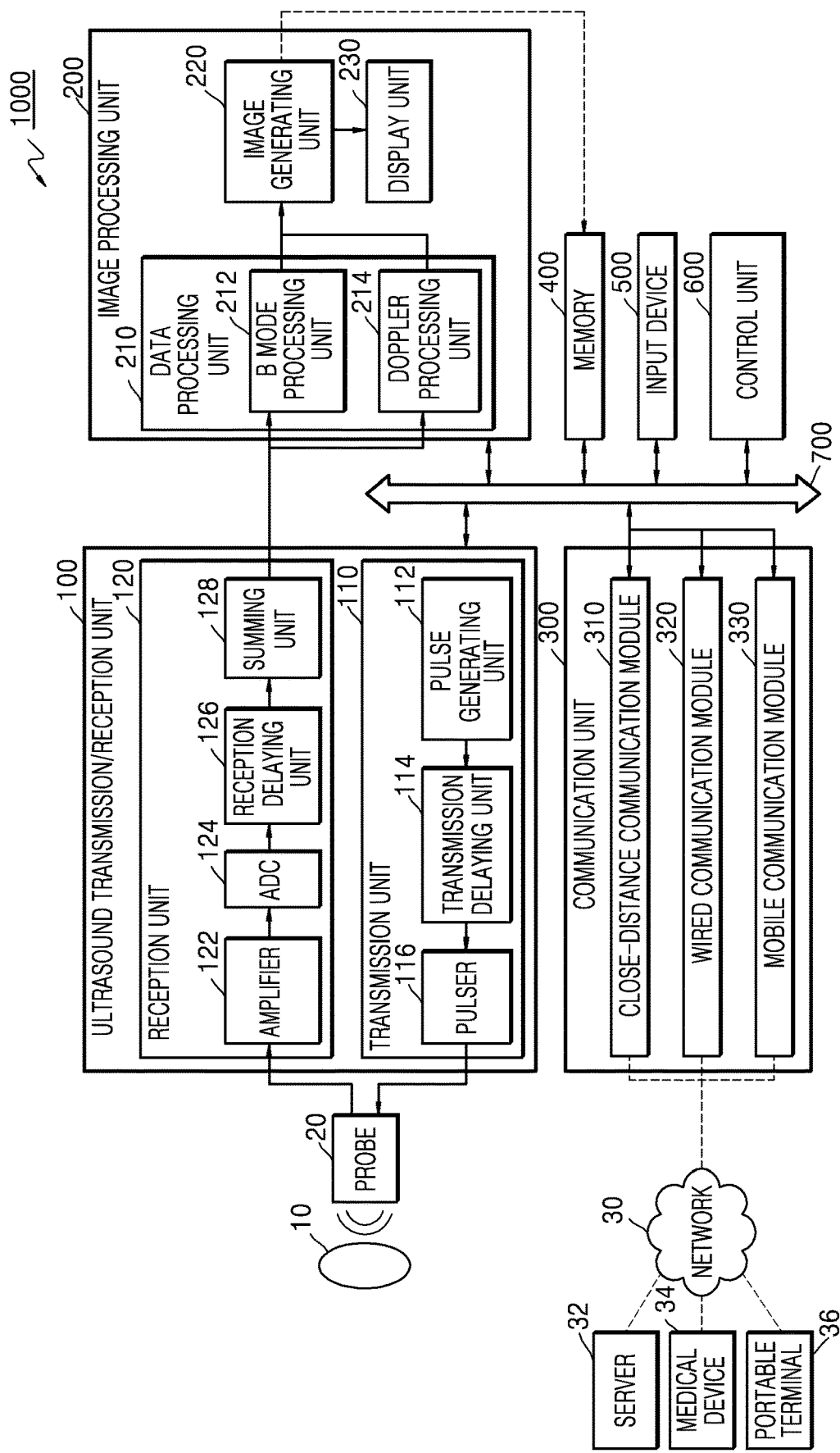
FIG. 12 is a block diagram of an ultrasound apparatus according to another exemplary embodiment.

FIG. 12 is a block diagram of an ultrasound apparatus 1000 according to another exemplary embodiment.

Referring to FIG. 12, the ultrasound apparatus 1000 may further include a probe 20, an image processor 200, a communication module 300, and a memory 400, in addition to a ultrasound transceiver 100, a display unit 230, a user input unit 500, and a controller 600. The above-described elements may be connected to each other through a bus 700.

The ultrasound apparatus 1000 may be implemented in a portable type as well as a cart type. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound apparatus 1000 by wire or wirelessly, and the ultrasound apparatus 1000 may include a plurality of the probes 20 depending on an implementation type.

A transmitter 110 supplies a driving signal to the probe 20. The transmitter 110 includes a pulse generator 112, a transmission delaying unit 114, and a pulser 116. The pulse generator 112 generates pulses for forming transmission ultrasound waves based on a predetermined pulse repetition frequency (PRF), and the transmission delaying unit 114 delays the pulses by delay times necessary for determining transmission directionality. The pulses which have been delayed correspond to a plurality of piezoelectric vibrators included in the probe 20, respectively. The pulser 116 applies a driving signal (or a driving pulse) to the probe 20 based on timing corresponding to each of the pulses which have been delayed.

A receiver 120 generates ultrasound data by processing echo signals received from the probe 20. The receiver 120 may include an amplifier 122, an analog-to-digital converter (ADC) 124, a reception delaying unit 126, and a summing unit 128. The amplifier 122 amplifies echo signals in each channel, and the ADC 124 performs analog-to-digital conversion with respect to the amplified echo signals. The reception delaying unit 126 delays digital echo signals output by the ADC 124 by delay times necessary for determining reception directionality, and the summing unit 128 generates ultrasound data by summing the echo signals processed by the reception delaying unit 166.

The image processor 200 generates an ultrasound image by scan-converting ultrasound data generated by the ultrasound transceiver 100 and displays the ultrasound image. The ultrasound image may be not only a grayscale ultrasound image obtained by scanning an object in an amplitude (A) mode, a brightness (B) mode, and a motion (M) mode, but also a motion of an object may be displayed as a Doppler image. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 212 extracts B mode components from ultrasound data and processes the B mode components. An image generator 220 may generate an ultrasound image indicating signal intensities as brightness based on the extracted B mode components 212.

Similarly, a Doppler processor 214 may extract Doppler components from ultrasound data, and the image generator 220 may generate a Doppler image indicating a movement of an object as colors or waveforms based on the extracted Doppler components.

According to an embodiment, the image generator 220 may generate a three-dimensional (3D) ultrasound image via volume-rendering with respect to volume data and may also generate an elasticity image by imaging deformation of the object 10 due to pressure. Furthermore, the image generator 220 may display various pieces of additional information in an ultrasound image by using text and graphics. In addition, the generated ultrasound image may be stored in the memory 400.

In addition, the ultrasound apparatus 1000 may include two or more displays 1100 according to embodiments.

The communication module 300 is connected to a network 30 by wire or wirelessly to communicate with an external device or a server. The communication module 300 may exchange data with a hospital server or another medical apparatus in a hospital, which is connected thereto via a PACS. Furthermore, the communication module 300 may perform data communication according to the digital imaging and communications in medicine (DICOM) standard.

The communication module 300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 300 may receive information about a diagnosis history or medical treatment schedule of a patient from a server and utilizes the received information to diagnose the patient. Furthermore, the communication module 300 may perform data communication not only with a server or a medical apparatus in a hospital, but also with a portable terminal of a medical doctor or patient.

The communication module 300 is connected to the network 30 by wire or wirelessly to exchange data with a server 32, a medical apparatus 34, or a portable terminal 36. The communication module 300 may include one or more components for communication with external devices. For example, the communication module 1300 may include a local area communication module 310, a wired communication module 320, and a mobile communication module 330.

The local area communication module 310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 320 refers to a module for communication using electric signals or optical signals. Examples of wired communication techniques according to an embodiment may include communication via a twisted pair cable, a coaxial cable, an optical fiber cable, and an Ethernet cable.

The mobile communication module 330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 400 stores various data processed by the ultrasound apparatus 1000. For example, the memory 400 may store medical data related to diagnosis of an object, such as ultrasound data and an ultrasound image that are input or output, and may also store algorithms or programs which are to be executed in the ultrasound apparatus 1000.

The memory 400 may be any of various storage media, e.g., a flash memory, a hard disk drive, EEPROM, etc. Furthermore, the ultrasound apparatus 1000 may utilize web storage or a cloud server that performs the storage function of the memory 400 online.

The user input unit 1200 may further include various input means such as an electrocardiogram measurement module, a breath measurement module, a voice recognition sensor, a gesture recognition sensor, a fingerprint recognition sensor, an iris recognition sensor, a depth sensor, a distance sensor, etc.

All or some of the probe 20, the ultrasound transceiver 100, the image processor 200, the communication module 300, the memory 400, the user input unit 500, and the controller 600 may be implemented as software modules. However, embodiments of the present invention are not limited thereto, and some of the components stated above may be implemented as hardware modules. Furthermore, at least one selected from the ultrasound transceiver 100, the image processor 200, and the communication module 300 may be included in the controller 600. However, embodiments of the present invention are not limited thereto.

The method according to the exemplary embodiments may be implemented as computer readable codes in a computer readable medium. The computer readable recording medium may include a program instruction, a local data file, a local data structure, or a combination thereof. The computer readable recording medium may be specific to exemplary embodiments of the invention or commonly known to those of ordinary skill in computer software. The computer readable recording medium includes all types of recordable media in which computer readable data are stored. Examples of the computer readable recording medium include a magnetic medium, such as a hard disk, a floppy disk and a magnetic tape, an optical medium, such as a CD-ROM and a DVD, a magneto-optical medium, such as a floptical disk, and a hardware memory, such as a ROM, a RAM and a flash memory, specifically configured to store and execute program instructions. Furthermore, the computer readable recording medium may be implemented in the form of a transmission medium, such as light, wire or waveguide, to transmit signals which designate program instructions, local data structures and the like. Examples of the program instruction include machine code, which is generated by a compiler, and a high level language, which is executed by a computer using an interpreter and so on.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An ultrasound apparatus comprising:
   an ultrasound transceiver that transmits an ultrasound signal to an object and receives an ultrasound echo signal reflected from the object;
   a controller that detects a change amount of a diameter of a blood vessel of the object during a period of a heartbeat of the object, based on the ultrasound echo signal and calculates a blood pressure graph showing a blood pressure of the object based on the detected change amount of the diameter;
   a display that displays the blood pressure graph and positions of a plurality of inflection points on the blood pressure graph; and
   a user input unit that receives a user input which selects a first inflection point from the plurality of inflection points,
   wherein the controller calculates a stiffness of the blood vessel, based on a difference between a maximum blood pressure in the blood pressure graph and a blood pressure corresponding to the first inflection point and controls the display to display the calculated stiffness, and
   wherein the controller, when a user input is received, selects a second inflection point which is adjacent to the first inflection point from the plurality of inflection points, calculates a second stiffness of the blood vessel, based on a difference between the maximum blood pressure in the blood pressure graph and a blood pressure corresponding to the second inflection point and controls the display to display the calculated second stiffness.

2. The ultrasound apparatus of claim 1, wherein the controller acquires an in-systole maximum blood pressure and a diastole blood pressure of the object, calculates a diameter change graph showing a time-based change amount of the diameter, based on the detected change amount of the diameter, and converts the diameter change graph to the blood pressure graph by expanding the diameter change graph, based on the acquired in-systole maximum blood pressure and diastole blood pressure.

3. The ultrasound apparatus of claim 1, wherein the display displays a speed graph of the change amount of the diameter on the blood pressure graph.

4. The ultrasound apparatus of claim 3, wherein the controller calculates a diameter change graph showing a time-based change amount of the diameter, based on the detected change amount of the diameter and differentiates the diameter change graph to calculate the speed graph of the change amount of the diameter.

5. The ultrasound apparatus of claim 3, wherein the display displays time points of the plurality of inflection points in the blood pressure graph, on the speed graph of the change amount of the diameter.

6. The ultrasound apparatus of claim 3, wherein,
   the controller determines time points, in which a slope of the speed graph of the change amount of the diameter becomes 0, as time point in which the plurality of inflection points in the blood pressure graph are positioned, and
   the display displays determined time points, on the speed graph of the change amount of the diameter.

7. The ultrasound apparatus of claim 1, wherein,
   the display displays a reference line indicating the first inflection point, and when a user input which moves the reference line to the right or the left is received, the display moves the reference line to the second inflection point from the first inflection point.

8. The ultrasound apparatus of claim 3, wherein the display adjusts and displays at least one selected from a time scale and a size scale of the speed graph of the change amount of the diameter, based on a user input which changes a scale of the speed graph of the change amount of the diameter.

9. A method of calculating a stiffness of a blood vessel, the method comprising:
- transmitting an ultrasound signal to an object and receiving an ultrasound echo signal reflected from the object;
- detecting a change amount of a diameter of a blood vessel of the object during a period of a heartbeat of the object, based on the ultrasound echo signal;
- calculating a blood pressure graph showing a blood pressure of the object based on the detected change amount of the diameter;
- displaying the blood pressure graph and positions of a plurality of inflection points on the blood pressure graph;
- receiving a user input which selects a first inflection point from the plurality of inflection points; and
- calculating a stiffness of the blood vessel, based on a difference between a maximum blood pressure in the blood pressure graph and a blood pressure corresponding to the first inflection point;
- displaying the calculated stiffness;
- selecting a second inflection point which is adjacent to the first inflection point from the plurality of inflection points, when a user input is received;
- calculating a second stiffness of the blood vessel, based on a difference between the maximum blood pressure in the blood pressure graph and a blood pressure corresponding to the second inflection point; and
- displaying the calculated second stiffness.

10. The method of claim 9, further comprising acquiring an in-systole maximum blood pressure and a diastole blood pressure of the object,
wherein the displaying of the blood pressure graph comprises:
calculating a diameter change graph showing a time-based change amount of the diameter, based on the detected change amount of the diameter; and
converting the diameter change graph to the blood pressure graph by expanding the diameter change graph, based on the acquired in-systole maximum blood pressure and diastole blood pressure.

11. The method of claim 9, further comprising displaying a speed graph of the change amount of the diameter on the blood pressure graph.

12. The method of claim 11, wherein the displaying of the speed graph comprises:
- calculating a diameter change graph showing a time-based change amount of the diameter, based on the detected change amount of the diameter;
- differentiating the diameter change graph to calculate the speed graph of the change amount of the diameter, and
- displaying the calculated speed graph of the change amount of the diameter.

13. The method of claim 11, wherein the displaying of the blood pressure graph and the positions of the plurality of inflection points comprises displaying time points of the plurality of inflection points in the blood pressure graph, on the speed graph of the change amount of the diameter.

14. The method of claim 11, wherein the displaying of the blood pressure graph and the positions of the plurality of inflection points comprises:
- determining time points, in which a slope of the speed graph of the change amount of the diameter becomes 0, as time points in which the plurality of inflection points in the blood pressure graph are positioned; and
- displaying the determined time points, on the speed graph of the change amount of the diameter.

15. The method of claim 9, further comprising:
- displaying a reference line indicating the first inflection point;
- receiving a user input which moves the reference line to the right or the left; and
- moving the reference line to the second inflection point adjacent from the first inflection point, based on the user input.

16. The method of claim 11, wherein the displaying of the speed graph comprises adjusting at least one selected from a time scale and a size scale of the speed graph of the change amount of the diameter, based on a user input which changes a scale of the speed graph of the change amount of the diameter.

* * * * *